United States Patent [19]
Roe et al.

[11] 3,966,946

[45] June 29, 1976

[54] 1,4-DIHYDROPYRIDINE COMPOUNDS IN TREATING HYPERTENSION

[75] Inventors: Anthony Maitland Roe, Hatfield; Robert Antony Slater, Letchworth, both of England; Bernard Loev, Broomall, Pa.

[73] Assignee: Smith Kline & French Laboratories Limited, Welwyn Garden City, England

[22] Filed: July 8, 1975

[21] Appl. No.: 594,188

Related U.S. Application Data

[63] Continuation-in-part of Ser. No. 476,346, June 5, 1974, Pat. No. 3,910,937.

[30] Foreign Application Priority Data

June 12, 1973 United Kingdom............... 27793/73

[52] U.S. Cl. ............................................. 424/263

[51] Int. Cl.$^2$......................................... A61K 31/44
[58] Field of Search................................... 424/263

[56] References Cited
OTHER PUBLICATIONS

Chem. Abst. – vol. 78 – 92394 (1973).
Chem. Abst. – vol. 70 – 87580 (1969).
Chem. Abst. – vol. 70 – 96641 (1969).

*Primary Examiner*—Stanley J. Friedman
*Attorney, Agent, or Firm*—Joan S. Keps; Richard D. Foggio; William H. Edgerton

[57] ABSTRACT

The compounds are 1,4-dihydropyridines having antihypertensive activity. A particular compound of this invention is 1,4-dihydro-2,6-dimethyl-4-(2-trifluoromethylphenyl)pyridine-3,5-dicarboxylic acid bis-(2-hydroxyethyl)ester.

10 Claims, No Drawings

1,4-DIHYDROPYRIDINE COMPOUNDS IN TREATING HYPERTENSION

This application is a continuation-in-part of Ser. No. 476,346, filed June 5, 1975, now U.S. Pat. No. 3,910,937.

This invention relates to 1,4-dihydropyridine compounds to methods for their preparation and to pharmaceutical compositions comprising these compounds.

The 1,4-dihydropyridine compounds of the present invention are useful as water-soluble antihypertensive agents which act primarily as precapillary vasodilators.

Throughout the present specification, by the term "lower alkyl" we mean an alkyl group containing from 1 to 4 carbon atoms.

According to the present invention we provide compounds of the following general formula I:

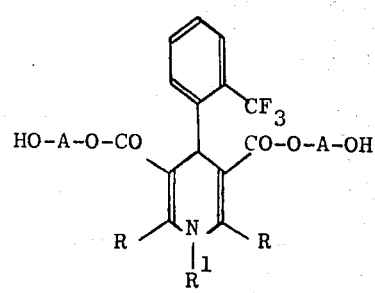

wherein R is a lower alkyl, $R^1$ is hydrogen or methyl, and A is a straight or branched alkylene chain the backbone of which contains from 2 to 4 carbon atoms.

A particular useful compound is that wherein each R is methyl, $R^1$ is hydrogen and A is 1,2-ethylene.

The compounds of our invention may be produced by a process wherein 2-trifluoromethylbenzaldehyde is reacted with an acyl fatty acid ester of the Formula II:

R — CO — CH$_2$COO — A — OQ

FORMULA II wherein R and A have the above significance and Q is hydrogen or a protecting group such as benzyl, in the presence of ammonia or a lower alkyl amine. This reaction may be carried out in a solvent such as ethanol under reflux conditions. The protecting group, if used, may then be removed by suitable means e.g., by hydrogenolysis in the case of a benzyl protecting group, to give the required compound of Formula I.

In an alternative process the 2-trifluoromethylbenzaldehyde is reacted with a compound of the Formula III:

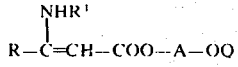

$$R-\overset{\overset{NHR^1}{|}}{C}=CH-COO-A-OQ$$

FORMULA III wherein R, $R^1$ and A have the same significance as in Formula I and Q has the same significance as in Formula II. As in the first mentioned process, any protecting group will of course be removed to give the required compound. A solvent such as acetic acid or ethanol may also be used.

Compounds of Formula I wherein $R^1$ is methyl may also be produced by treatment in the presence of a base such as sodium hydride of a compound of Formula I wherein $R^1$ is hydrogen with a methyl halide. This reaction may be carried out in a solvent such as dimethylformamide.

The pharmacological activity of our compounds may be demonstrated in conscious cannulated normotensive dogs wherein dose-dependent hypotension results from the oral administration of from 2.5 to 20 mg/kg of our compounds, and in rats wherein an increased flow rate is observed in the hindquarters, perfused at constant pressure, on the intravenous administration of 0.8 mg/kg of our compounds.

Our invention also provides pharmaceutical compositions comprising a compound of Formula I together with a pharmaceutically acceptable diluent or carrier. Advantageously the compositions will be made up in a dosage unit form appropriate to the desired mode of administration. The pharmaceutical carrier employed may be, for example, either a solid or a liquid. Exemplary of solid carriers are lactose, terra alba, sucrose, talc, gelatin, agar, pectin, acacia, magnesium stearate and stearic acid. Exemplary of liquid carriers are syrup, peanut oil, olive oil and water, the latter being particularly preferred because of the water solubility of the compounds of Formula I and because of the great utility for injectible use of such aqueous solutions. Other pharmacologically active compounds may in certain cases be included in the pharmaceutical compositions.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, solf gelatin capsule or a sterile injectible liquid, preferably water, which may be prepared in an ampoule.

The pharmaceutical compositions are prepared by conventional techniques involving procedures such as mixing, granulating and compressing or dissolving the ingredients as appropriate to the desired preparation. The active ingredients will be present in the composition in an effective amount to produce the required anti-hypertensive effect. The route of administering may be orally or parenterally e.g., sub-cutaneously or intravenously.

Advantageously the composition will be made up in a dosage form appropriate to the desired mode of administration, for example, as a tablet, capsule or injectable solution.

Preferably, the pharmaceutical compositions of this invention contain a compound of Formula I in an amount of from about 5 mg to about 500 mg, most preferably from about 25 mg to about 250 mg, per dosage unit.

The method of producing anti-hypertensive activity, which is also an object of this invention, comprises administering internally to an animal an effective amount of a compound of Formula I. The active ingredient will preferably be administered in dosage unit form as described above. Preferably, the active ingredient will be administered in a total daily dosage of from about 5 mg to about 2000 mg, most preferably from about 50 mg to about 1000 mg. The active ingredient will preferably be administered in equal doses 1 to 4 times per day. When the administration is carried out as described above, antihypertensive activity is produced.

One skilled in the art will recognize that in determining the amounts of the active ingredient in the claimed compositions and used in the claimed methods, the activity of the chemical ingredient as well as the size of the host animal must be considered.

The invention is illustrated but in no way limited by the following examples:

EXAMPLE 1.

Preparation of
1,4-dihydro-2,6-dimethyl-4-(2-trifluoromethylphenyl)-pyridine-3,5-dicarboxylic acid bis (2-hydroxyethyl)ester.

i. A mixture of acetoacetic ester (13.0 g) and 2-benzyloxyethanol (22.0 g) was stirred under reflux for 30 minutes. Distillation under vacuum yielded the crude product (21.5 g) which on re-distillation gave, as a colourless oil, acetoacetic acid 2-benzyloxyethyl ester (17.2 g), b.p. 124°C/0.1 mm.

ii. A mixture of acetoacetic acid 2-benzyloxyethyl ester (30 g), o-trifluoromethyl benzaldehyde (11.2 g) and concentrated ammonia (8.0 ml of density 0.88) in ethanol (100 ml) was stirred under reflux for 24 hours and then poured into ice and water. The yellow oil which precipitated was separated, and solidified on addition of ethanol. Recrystallisation from ethanol gave 1,4-dihydro-2,6-dimethyl-4-(2-trifluoromethylphenyl)pyridine 3,5-dicarboxylic acid bis-(2-benzyloxyethyl)ester (10.4 g), as white crystals m.p. 141°–142°C.

iii. The bis-benzyl ether, produced in (ii) above, (8 g) was dissolved in ethanol and hydrogenated over palladium charcoal, Evaporation to dryness of the filtrate, produced on the removal of the catalyst, and recrystallisation of the residue, first from isopropyl acetate and then from ethanol gave 1,4-dihydro-2,6-dimethyl-4-(2-trifluoromethylphenyl)pyridine-3,5-dicarboxylic acid bis-(2-hydroxyethyl) ester (4.6 g) m.p. 125°–127°.

EXAMPLE 2

Preparation of
1,4-dihydro-1,2,6-trimethyl-4-(2-trifluoromethylphenyl)pyridine-3,5-dicarboxylic acid bis (2-hydroxyethyl)ester.

i. To a stirred solution of 1,4-dihydro-2,6-dimethyl-4-(2-trifluoromethylphenyl)pyridine-3,5-dicarboxylic acid bis (2-benzyloxethyl)ester (18.2 g.) in dry dimethylformamide (100 ml) was added in portions, sodium hydride (1.38 g. of a 60% dispersion in oil). When the mixture had been stirred for a further 60 minutes at room temperature methyl iodide (30 ml) was added and stirring was continued for another hour. The reaction mixture was then treated with saturated ammonium chloride solution (150 ml) and the resulting solution extracted with ether. Evaporation of the dried extracts gave an oil which was purified by column chromatography to give as a pale yellow oil 1,4-dihydro-1,2,6-trimethyl-4-(2-trifluoromethylphenyl)pyridine-3,5-dicarboxylic acid bis(2-benzyloxyethyl)ester (6.0 g).

ii. The bis-benzyl ether produced in (i) above (5.7 g) was hydrogenated over palladium-charcoal as described in Example 1 to give, after purification by column chromatography and recrystallisation from aqueous ethanol, 1,4-dihydro-1,2,6-trimethyl-4-(2-trifluoromethylphenyl)pyridine-3,5-dicarboxylic acid bis (2-hydroxyethyl)ester (1.1 g) as colourless crystals m.p. 120°–122°C.

EXAMPLE 3

Preparation of
1,4-dihydro-2,6-dimethyl-4-(2-trifluoromethylphenyl)-pyridine-3,5-dicarboxylic acid bis(3-hydroxy-2-propyl)ester i. A mixture of acetoacetic ester (19.0 g) and 3-benzyloxy-2-propanol (32.0 g) were stirred under reflux for 2 hours. Fractional distillation under vacuum gave, as a colourless oil, acetoacetic acid (3-benzyloxy-2-propyl) ester (15.2 g), b.p. 130°–135°C/0.1 mm.

ii. A mixture of acetoacetic acid (3-benzyloxy-2-propyl) ester (23.8 g), o-trifluoromethylbenzaldehyde (8.7 g.) and concentrated ammonia (10.0 ml. of density 0.88) in ethanol (200 ml) was stirred under reflux for 24 hours and then poured into ice and water. The yellow oil which precipitated was separated and purified by column chromatography to give as a pale yellow oil 1,4-dihydro-2,6-dimethyl-4-(2-trifluoromethylphenyl)-pyridine-3,5-dicarboxylic acid bis(3-benzyloxy-2-propyl)ester (24.8 g).

iii. The bis-benzyl ether produced in (ii) above (10.6 g) was dissolved in ethanol and hydrogenated over palladiumcharcoal as described in Example 1 to give, after purification by column chromatography and crystallisation 1,4-dihydro-2,6-dimethyl-4-(2-trifluoromethylphenyl)pyridine-3,5-dicarboxylic acid bis(3-hydroxy-2-propyl)ester.

EXAMPLE 4

Preparation of
1,4-dihydro-2,6-dipropyl-4-(2-trifluoromethylphenyl)-pyridine-3,5-dicarboxylic acid bis (2-hydroxyethyl)ester Reaction of butyroacetic ester and 2-benzyloxyethanol by the procedure of Example 1(i) gives butyroacetic acid 2-benzyloxyethyl ester which, when used as the starting material in the process of Example 1(ii) gives the bis-benzyl ether of the title compound. Hydrogenolysis of this ether according to the procedure of Example 1(iii) yields the title compound.

EXAMPLE 5

Preparation of
1,4-dihydro-2,6-dimethyl-4-(2-trifluoromethylphenyl)-pyridine-3,5-dicarboxylic acid bis (4-hydroxybutyl)ester.

Reaction of acetoacetic ester and 4-benzyloxybutanol according to the procedure of Example 1(i) gives acetoacetic acid 4-benzyloxybutyl ester which, when used as the starting material in the process of Example 1(ii) gives the bisbenzyl ether of the title compound. Hydrogenolysis of this ether by the procedure of Example 1(iii) yields the title compound.

EXAMPLE 6

| Ingredients | Amounts |
|---|---|
| 1,4-Dihydro-2,6-dimethyl-4-(2-trifluoromethylphenyl)pyridine-3,5-dicarboxylic acid bis (2-hydroxyethyl)ester | 150 mg |
| Sucrose | 25 mg |
| Starch | 15 mg |
| Talc | 5 mg |
| Stearic acid | 3 mg |

The active ingredient is mixed with the sucrose and the resulting mixture is granulated with 10% gelatin solution. The granules are screened, dried and mixed with starch, talc and stearic acid, screened and compressed into a tablet.

EXAMPLE 7

| Ingredients | Amounts |
|---|---|
| 1,4-Dihydro-2,6-dimethyl-4-(2-trifluoromethylphenyl)pyridine-3,5-dicarboxylic acid bis (3-hydroxy-2-propyl)ester | 150 mg |
| Lactose | 75 mg |

The ingredients are mixed, screened and filled into a hard gelatin capsule.

The compositions prepared as in Examples 6 and 7 are administered orally to hypertensive subjects within the dose range given hereabove.

What we claim is:

1. A pharmaceutical composition having anti-hypertensive activity, in dosage unit form, comprising a pharmaceutical carrier and in an effective amount to produce said activity a 1,4-dihydropyridine compound of the formula:

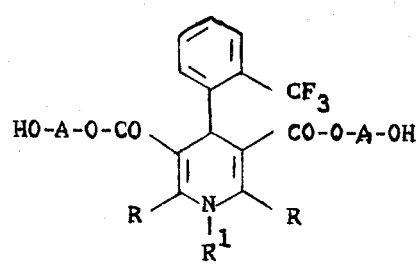

wherein R is lower alkyl, $R^1$ is hydrogen or methyl and A is a straight or branched alkylene chain the backbone of which contains from 2 to 4 carbon atoms.

2. A pharmaceutical composition of claim 1 in which the 1,4-dihydropyridine compound is 1,4-dihydro-2,6-dimethyl-4-(2-trifluoromethylphenyl)pyridine-3,5-dicarboxylic acid bis (2-hydroxyethyl)ester.

3. A pharmaceutical composition of claim 1 in which the 1,4-dihydropyridine compound is 1,4-dihydro-1,2,6-trimethyl-4-(2-trifluoromethylphenyl)pyridine-3,5-dicarboxylic acid bis (2-hydroxyethyl)ester.

4. A pharmaceutical composition of claim 1 in which the 1,4-dihydropyridine compound is 1,4-dihydro-2,6-dimethyl-4-(2-trifluoromethylphenyl)pyridine-3,5-dicarboxylic acid bis (3-hydroxy-2-propyl)ester.

5. A pharmaceutical composition of claim 1 in which the 1,4-dihydropyridine compound is present in an amount of from about 5 mg to about 500 mg.

6. A method of producing anti-hypertensive activity which comprises administering internally to an animal in an effective amount to produce said activity a 1,4-dihydropyridine compound of the formula:

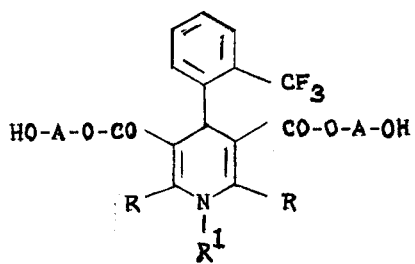

wherein R is lower alkyl, $R^1$ is hydrogen or methyl and A is a straight or branched alkylene chain the backbone of which contains from 2 to 4 carbon atoms.

7. A method of claim 6 in which the 1,4-dihydropyridine compound is 1,4-dihydro-2,6-dimethyl-4-(2-trifluoromethylphenyl)pyridine-3,5-dicarboxylic acid bis (2-hydroxyethyl)ester.

8. A method of claim 6 in which the 1,4-dihydropyridine compound is 1,4-dihydro-1,2,6-trimethyl-4-(2-trifluoromethylphenyl)pyridine-3,5-dicarboxylic acid bis (2-hydroxyethyl)ester.

9. A method of claim 6 in which the 1,4-dihydropyridine compound is 1,4-dihydro-2,6-dimethyl-4-(2-trifluoromethylphenyl)pyridine-3,5-dicarboxylic acid bis (3-hydroxy-2-propyl)ester.

10. A method of claim 6 in which the 1,4-dihydropyridine compound is administered in a daily dosage of from about 5 mg to about 2000 mg.

* * * * *

UNITED STATES PATENT OFFICE
CERTIFICATE OF CORRECTION

PATENT NO. : 3,966,946
DATED : June 29, 1976
INVENTOR(S) : Anthony Maitland Roe, Robert Antony Slater and Bernard Loev It is certified that error appears in the above-identified patent and that said Letters Patent are hereby corrected as shown below:

Column 1, line 5, "June 5, 1975" should read -- June 5, 1974 -- .

Signed and Sealed this

Twelfth Day of October 1976

[SEAL]

Attest:

RUTH C. MASON
Attesting Officer

C. MARSHALL DANN
Commissioner of Patents and Trademarks